US008175347B2

(12) United States Patent  
Hirakawa (10) Patent No.: US 8,175,347 B2  
(45) Date of Patent: May 8, 2012

(54) IN VIVO IMAGE DISPLAY APPARATUS, RECEIVING APPARATUS, AND IMAGE DISPLAY SYSTEM USING SAME AND IMAGE DISPLAY METHOD THEREOF

(75) Inventor: Katsumi Hirakawa, Sagamihara (JP)

(73) Assignee: Olympus Medical Systems Corp. (JP)

( * ) Notice: Subject to any disclaimer, the term of this patent is extended or adjusted under 35 U.S.C. 154(b) by 1248 days.

(21) Appl. No.: 11/563,060

(22) Filed: Nov. 24, 2006

(65) Prior Publication Data

US 2007/0173714 A1     Jul. 26, 2007

(30) Foreign Application Priority Data

Nov. 24, 2005   (JP) .................................. 2005-339325

(51) Int. Cl.
*G06K 9/00* (2006.01)
(52) U.S. Cl. ....................................................... 382/128
(58) Field of Classification Search .................. 382/128, 382/131, 132; 600/118, 160, 459, 476–478
See application file for complete search history.

(56) References Cited

U.S. PATENT DOCUMENTS

| 7,755,503 | B2 * | 7/2010 | Bonorden et al. ......... 340/686.1 |
| 2004/0111011 | A1 | 6/2004 | Uchiyama et al. |
| 2004/0249291 | A1 * | 12/2004 | Honda et al. ................. 600/476 |
| 2005/0075551 | A1 | 4/2005 | Horn et al. |

FOREIGN PATENT DOCUMENTS

| AU | 2004233674 | 11/2004 |
| JP | 2003-19111 | 1/2003 |
| JP | 2005-296044 | 10/2005 |
| JP | 2005-304512 | 11/2005 |
| JP | 2005-319095 | 11/2005 |
| WO | WO 2004/096025 | 11/2004 |
| WO | WO 2005/031650 | 4/2005 |

OTHER PUBLICATIONS

Extended European Search Report dated Jun. 24, 2009 in corresponding European Patent Application No. EP 06 83 3175 (English language).
International Search Report and Written Opinion dated Apr. 27, 2007 issued in corresponding PCT Application No. PCT/JP2006/323353.
Chinese Office Action dated Sep. 25, 2009 in corresponding Chinese Patent Application No. 2006800440024 (in Chinese language).

* cited by examiner

*Primary Examiner* — Claire X Wang
(74) *Attorney, Agent, or Firm* — Ostrolenk Faber LLP (57) ABSTRACT

An object of the present invention is to alleviate an image diagnosing work in a work station or the like. In a viewer 7 for displaying, on a display unit 11, image data based on a radio signal transmitted from a capsule endoscope to be inserted into a subject, an image processing circuit 35 processes image data received from a receiving apparatus 5 via an interface 34, so as to produce an image processing result of the image data, and further, a control unit 38 displays the image and the image processing result on the display unit 11 in real time, so as to enable a body-cavity image to be observed with reference to the image processing result.

4 Claims, 8 Drawing Sheets

IN VIVO IMAGE DISPLAY APPARATUS, RECEIVING APPARATUS, AND IMAGE DISPLAY SYSTEM USING SAME AND IMAGE DISPLAY METHOD THEREOF

CROSS-REFERENCE TO RELATED APPLICATIONS

This application is based upon and claims the benefit of priority from Japanese Patent Application No. 2005-339325, filed Nov. 24, 2005, the entire contents of which are incorporated herein by reference.

BACKGROUND OF THE INVENTION

1. Field of the Invention

The invention relates to an in-vivo image display apparatus which displays, on a display, an image based on a radio signal transmitted from an in-vivo image acquiring apparatus such as a capsule endoscope to be inserted into a subject, a receiving apparatus, an image display system using the in-vivo image display apparatus and the receiving apparatus, and an image display method.

2. Description of the Related Art

In recent years, a capsule endoscope equipped with an image pick-up function and a radio communication function has appeared in the field of endoscope. Such a capsule endoscope is swallowed by a subject through a mouth for the purpose of observation (examination) before the capsule endoscope is moved through the inside of organs (body cavities) such as esophagus, stomach, and small intestine according to peristalsis during an observation period until the capsule endoscope is naturally discharged from a biological body (human body) of the subject. In this manner, the capsule endoscope sequentially picks up images at a predetermined image pick-up rate by utilizing the image pick-up function.

Image data picked up by the capsule endoscope in the body cavity during the observation period during which the capsule endoscope is moved through the inside of the organs is transmitted in sequence to the outside of the subject by the radio communication function such as radio communications, and stored in a memory housed in a receiving apparatus disposed outside. If the subject carries the receiving apparatus equipped with the radio communication function and a memory function, the subject can freely move without any restriction even during the observation period after he or she swallows the capsule endoscope until he or she discharges it (see Japanese Patent Application Laid-open (JP-A) No. 2003-19111).

For the reception of the image data, the receiving apparatus is generally so configured that a plurality of antennas for receiving an image signal to be transmitted from the capsule endoscope are dispersed outside the subject, and that a single antenna having a great reception strength is selectively switched, thereby receiving the image signal. JP-A No. 2003-19111, for example, discloses a receiving apparatus, which switches the reception by the plurality of antennas arranged outside the subject, and then, searches the position of the capsule endoscope inside the subject as a transmission source of the image signal based on electric field strength received by each of the antennas.

In such a capsule endoscope system, the image data accumulated in the memory of the receiving apparatus is transferred to a work station or the like after a series of image pick-up operations by the capsule endoscope is finished, and the user, i.e., a doctor or a nurse generally observes the images afterwards.

However, there is a large quantity of images to be observed since, for example, two frames are picked up by the capsule endoscope per second. Therefore, a doctor makes a diagnosis with much labor.

SUMMARY OF THE INVENTION

An object of the present invention is to solve at least the above described problems.

An in-vivo image display apparatus according to one aspect of the present invention includes a display unit which sequentially receives and displays image data acquired by an in-vivo image acquiring apparatus, and an identification data generator which can arbitrarily generates identification data which corresponds to the image data displayed on the display unit and can be recognized by another in-vivo image display apparatus.

A receiving apparatus according to another aspect of the present invention includes an identification data generator which sequentially receives image data acquired by an in-vivo image acquiring apparatus and can arbitrarily generate identification data which corresponds to the image data received and can be recognized in another in-vivo image display apparatus.

An image display system according to still another aspect of the present invention includes a receiving apparatus which sequentially receives image data acquired by an in-vivo image acquiring apparatus and stores the image data received in a recording unit, and an in-vivo image display apparatus which sequentially takes in the image data from the receiving apparatus, and sequentially displays the image data taken-in on a display unit, wherein at least one of the receiving apparatus and the in-vivo image display apparatus includes an identification data generator capable of arbitrarily generating identification data which corresponds to the image data displayed on the display unit and can be recognized in another in-vivo image display apparatus.

An image display method according to still another aspect of the invention includes the steps of sequentially displaying image data sequentially received by a receiving apparatus from an in-vivo image acquiring apparatus on a display unit of a in-vivo image display apparatus, arbitrarily marking image data suspected of showing pathological lesion out of the image data displayed on the display unit, and storing the image data marked in a recording unit in the receiving apparatus.

An in-vivo image display apparatus according to still another aspect of the invention is communicatively connected to a receiving apparatus, which sequentially receives image data acquired by an in-vivo image acquiring apparatus, via a cable, detects a connection with the receiving apparatus via the cable, and sequentially transmits the image data from the in-vivo image acquiring apparatus to the in-vivo image display apparatus.

A receiving apparatus according to still another aspect of the invention is communicatively connected to an in-vivo image display apparatus, which sequentially displays image data acquired by an in-vivo image acquiring apparatus on a display unit, via a cable, detects a connection with the in-vivo image display apparatus via the cable, and sequentially transmits the image data from the in-vivo image acquiring apparatus to the in-vivo image display apparatus.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

A detailed description will be given below of exemplary embodiments of an in-vivo image display apparatus, a receiving apparatus, an image display system using the in-vivo image display apparatus and the receiving apparatus, and an image display method according to the present invention with reference to FIGS. 1 to 8. The invention is not limited to the preferred embodiments, and various modifications can be made without departing from the scope of the invention.

First Embodiment

Figure 1:
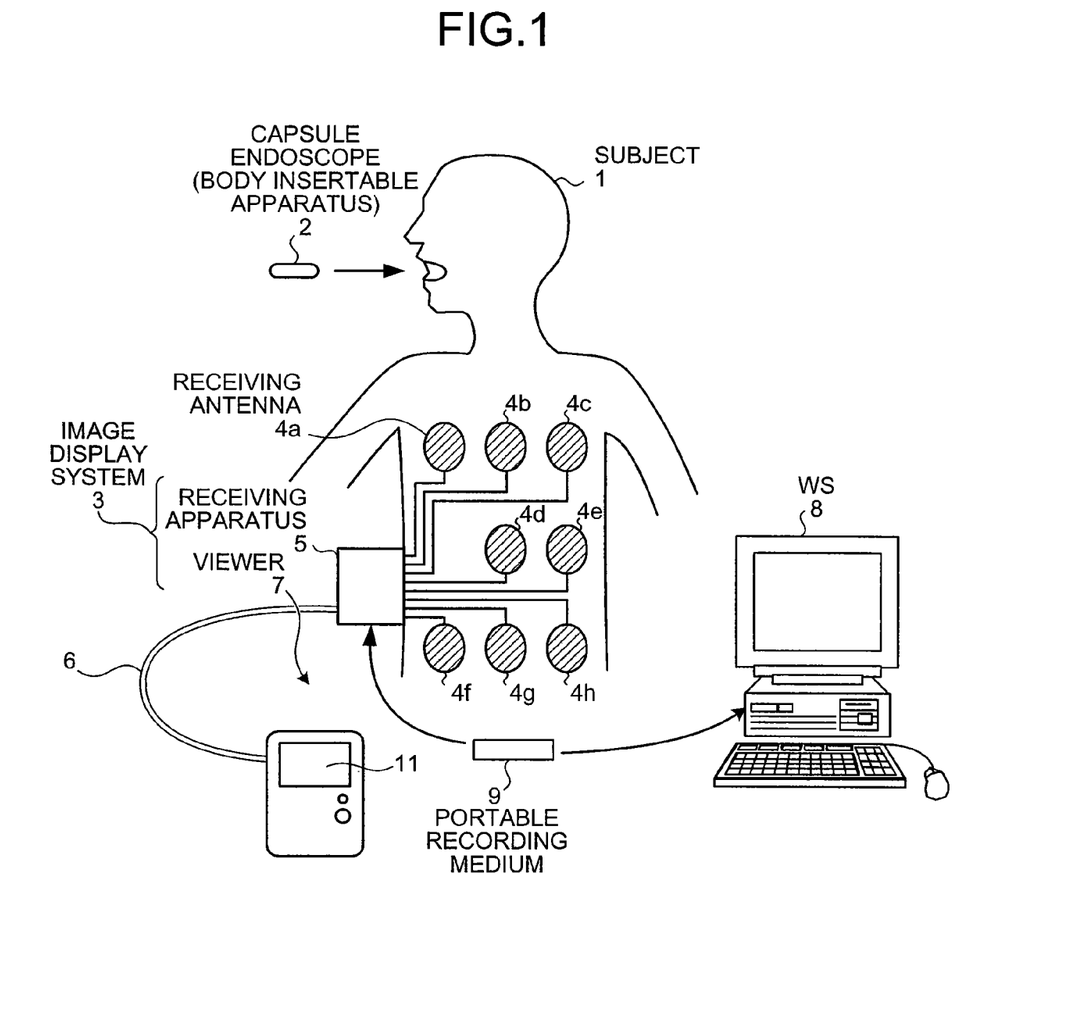
FIG. 1 is a schematic diagram of an overall configuration of a radio-type in-vivo information acquiring system which is a first embodiment of a portable in-vivo image display apparatus and a portable image display system according to the invention.
Figure 2:
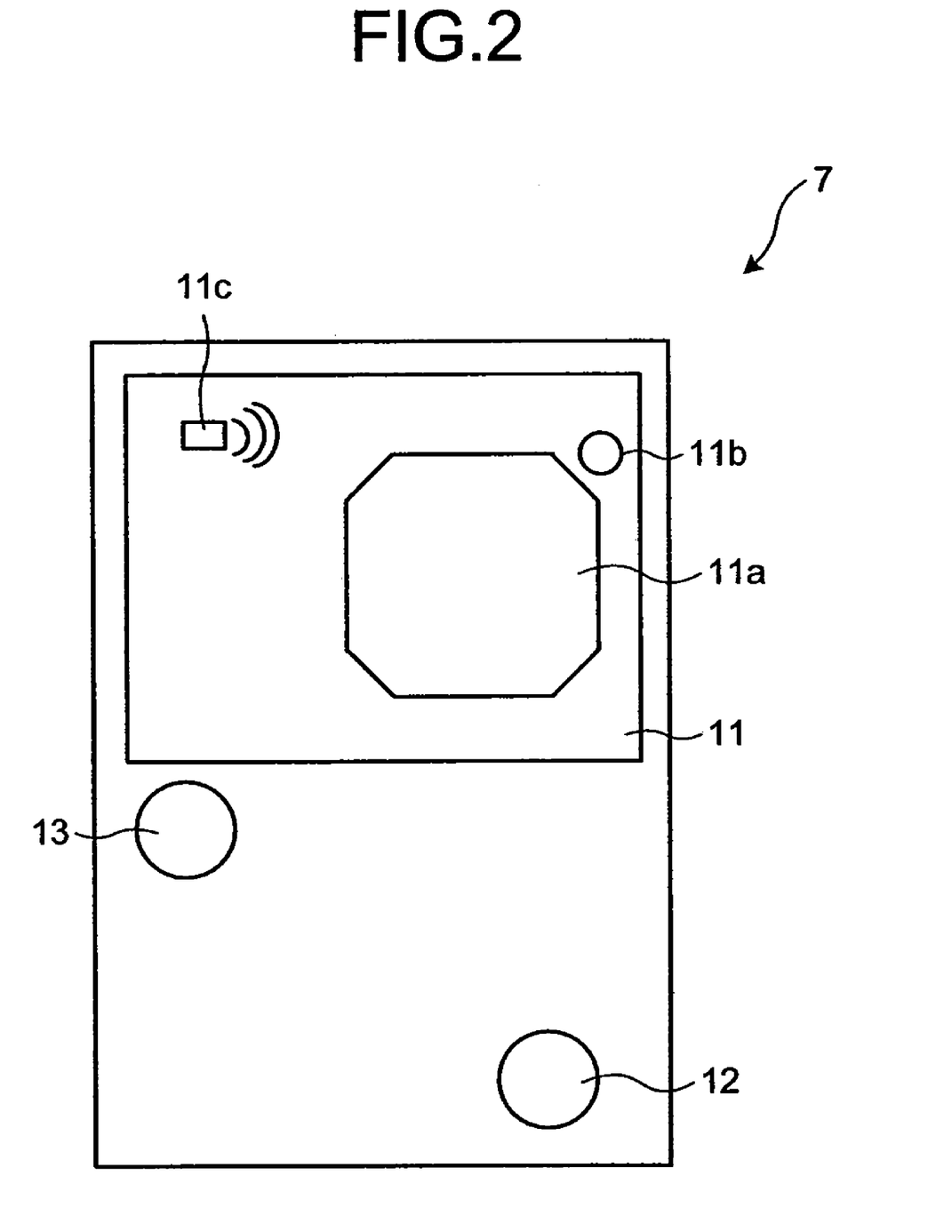
FIG. 2 is a schematic diagram illustrating the outside appearance of the in-vivo image display apparatus of FIG. 1.

FIG. 1 is a schematic diagram of an overall configuration of a radio-type in-vivo information acquiring system as a first preferred embodiment of a portable in-vivo image display apparatus and a portable image display system according to the invention, and FIG. 2 is a schematic diagram of an appearance of the in-vivo image display apparatus. The radio-type in-vivo information acquiring system includes a capsule endoscope as an example of an in-vivo image acquiring apparatus serving as a transmitter. In FIG. 1, the radio-type in-vivo information acquiring system is provided with an image display system 3 which is used for an image display and a reception process of a radio signal transmitted from a capsule endoscope 2 inserted into a subject 1. The image display system 3 includes a receiving apparatus 5, which is carried by the subject 1 during use to perform the reception process on a radio signal received via receiving antennas 4a to 4h, and a viewer 7, as the portable in-vivo image display apparatus, which is detachably connected to the receiving apparatus 5 via a viewer cable 6 to display an image picked up by the capsule endoscope 2 based on an electric signal output from the receiving apparatus 5.

The radio-type in-vivo information acquiring system in the first embodiment further includes a work station (abbreviated as a "WS": which is another in-vivo image display apparatus) 8 which displays a body-cavity image based on a video signal received by the image display system 3, and a portable recording medium 9 as a storage unit, through which data is transferred between the receiving apparatus 5 and the work station 8.

The capsule endoscope 2 is inserted into the subject 1 through a mouth of the subject 1, and has a function of radio-transmitting body-cavity image data acquired by, for example, a built-in pick-up mechanism to the outside of the subject 1. The receiving antennas 4a to 4h are dispersed and securely arranged at appropriate positions on an outer surface of a body of the subject 1. The receiving antennas 4a to 4h may be attached onto a receiving jacket which the subject 1 can wear, for example, so that the receiving antennas 4a to 4h are attached to the subject 1 when the subject 1 wears the receiving jacket. In this case, the receiving antennas 4a to 4h may be detachable from the jacket.

The work station 8 is adapted to display the body-cavity image or the like picked up by the capsule endoscope 2, and performs an image display based on data acquired by the portable recording medium 9, for example. Specifically, the work station 8 may be so configured as to directly display the image on a CRT display, a liquid crystal display, or the like. Alternatively, the work station 8 may be so configured as to output the image to another medium, like a printer.

The portable recording medium 9 is, for example, a compact flash (registered trademark) memory, and is detachably attached to the receiving apparatus 5 and the work station 8, and further, the portable recording medium 9 has such a structure that information can be output from or recorded into the portable recording medium 9 when the portable recording medium 9 is attached to the receiving apparatus 5 or the work station 8. In the first embodiment, the portable recording medium 9 is attached to a display in the work station 8 before the examination so that identification information such as an examination ID is stored in the portable recording medium 9. Immediately before the examination, the portable recording medium 9 is attached to the receiving apparatus 5, which reads out the identification information and registers the same therein. During the movement of the capsule endoscope 2 through the body cavity of the subject 1, the portable recording medium 9 is inserted into the receiving apparatus 5 attached to the subject 1, and records data (inclusive of the image data) transmitted from the capsule endoscope 2. And further, while the viewer 7 performs the image display, the portable recording medium 9 records information indicating an image processing result and information indicating a marking result described later, which are input from the viewer 7, in association with corresponding image data. Furthermore, after the discharge of the capsule endoscope 2 from the subject 1, that is, upon completion of the image pick-up inside the subject 1, the portable recording medium 9 is taken out of the receiving apparatus 5, and then, is inserted into the work station 8, which then reads the data recorded in the portable recording medium 9. For example, since the data is transferred between the receiving apparatus 5 and the work station 8 via the portable recording medium 9, the subject 1 can freely move during the image pick-up inside the body cavity, and further, the portable recording medium 9 contributes to shorten a time required for data transfer between the receiving apparatus 5 and the work station 8. The data may be transferred between the receiving apparatus 5 and the work station 8 by another recording device such as a hard disk built in the receiving apparatus 5, and the receiving apparatus 5 and the work station 8 may be connected to each other via a cable or by radio for data transfer between the receiving apparatus 5 and the work station 8.

The viewer 7 is of a portable type, which is formed in such a size that a user can grab by the hand, and has the function of displaying an image based on an electric signal output from the receiving apparatus 5. In order to implement the function, the viewer 7 is provided with a display unit 11 having a small-sized LCD for displaying an image, as shown in FIG. 2. The display unit 11 includes: an image display area 11a where an image taken from the receiving apparatus 5 is displayed; a predetermined display pattern, i.e., a circle-shape image mark 11b in the first embodiment, displayed as identification data to the right of and above the image display area 11a, in which the image is displayed, when the image obtained through image processing by an image processing circuit 35 described later shows possibility of pathological lesion such as hemorrhage; and another predetermined display pattern, i.e., a reception status mark 11c including a rectangle-like image and curves in the first embodiment, displayed to the left and above the image display area 11a so as to show a reception status. The above-described display patterns correspond to the images displayed in the image display area 11a, and further, are identification data which can be recognized in the work station 8. Examples of the identification data which can be recognized in the work station 8 include information indicating that the image data is suspected of showing pathological lesion such as the hemorrhage (information indicating an image processing result by the image processing circuit 35, described later), information on the reception status of the image data of an interior of the subject 1, and the like.

The viewer 7 is further provided with a power switch 12, and a marking button 13 serving as a marker for optionally marking the image displayed on the display unit 11. The marking button 13 is operated in marking the image data suspected of showing pathological lesion such as the hemorrhage. The operation of the marking button 13 enables the viewer 7 to optionally mark the image data suspected of showing pathological lesion such as the hemorrhage out of the image data of the subject 1 displayed on the display unit 11. Information indicating that the image data is marked through the operation of the marking button 13 (i.e., marking result) is one example of the identification data which can be recognized in the work station 8. Incidentally, though the receiving apparatus 5 and the viewer 7 are connected to each other via the viewer cable 6 in FIG. 1, they are not used in the connection state all the time. The viewer cable 6 is disconnected when a real-time observation is not performed based on images received via the receiving apparatus 5, and therefore, the subject 1 carries only the receiving apparatus 5.

Figure 3:
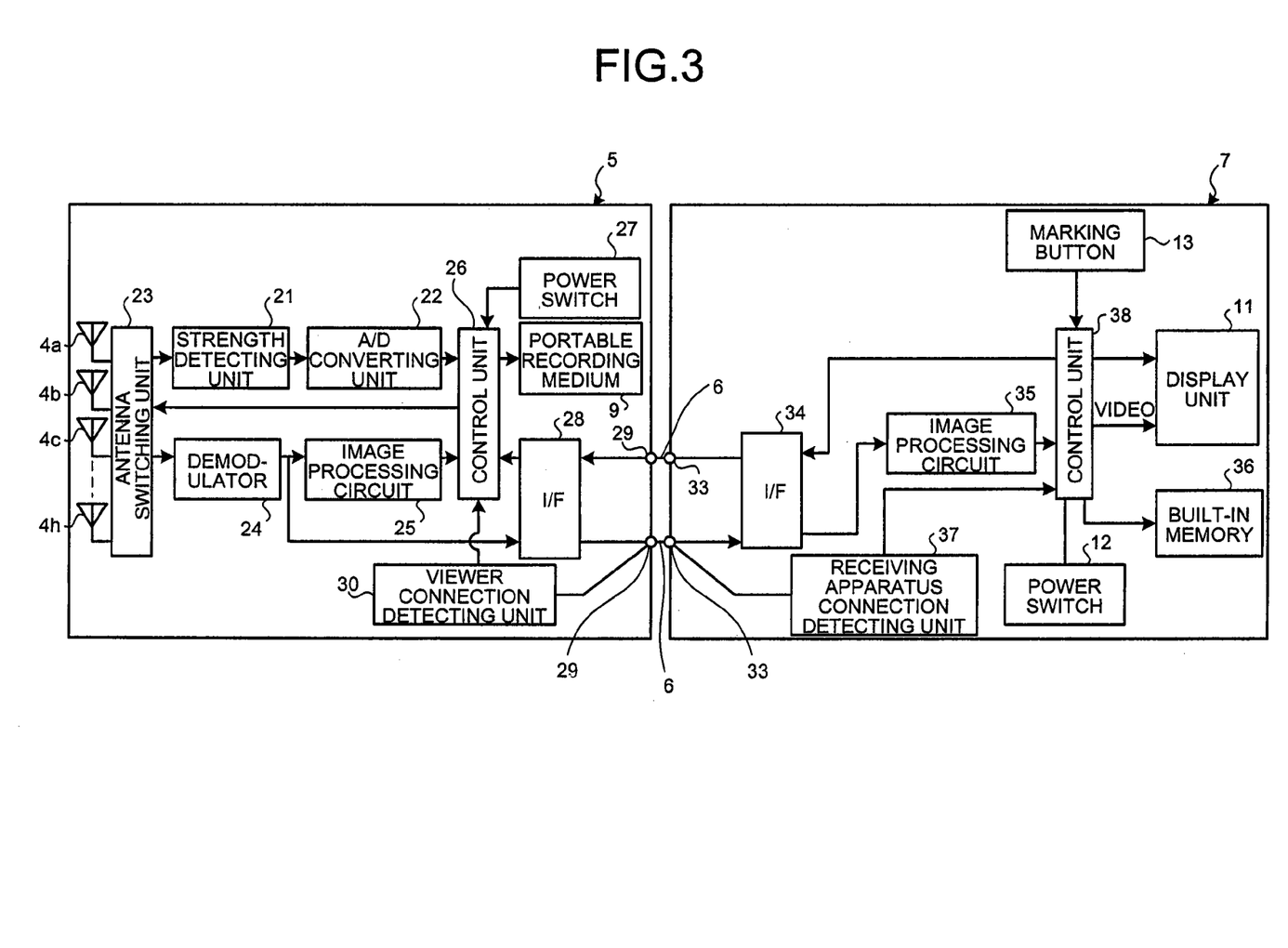
FIG. 3 is a schematic block diagram illustrating a constitutional example of a receiving apparatus and a viewer constituting a receiving system in the first embodiment.

Explanation will be made in detail on the configurations of the receiving apparatus 5 and the viewer 7. FIG. 3 is a schematic block diagram of an exemplary configuration of the receiving apparatus 5 and the viewer 7 constituting the image display system 3 of the first embodiment. The receiving apparatus 5 includes: a strength detecting unit 21 for detecting the reception strength based on a reception strength signal from each of the receiving antennas 4a to 4h; an A/D converting unit 22 for A/D-converting a detection result of the reception strength; and an antenna switching unit 23 for selecting one antenna having a highest reception strength out of the receiving antennas 4a to 4h based on the detection result of the A/D-converted reception strength. Moreover, the receiving apparatus 5 is provided with a demodulator 24 for performing a demodulation process on the radio signal received via one antenna selected by the antenna switching unit 23, and an image processing circuit 25 for performing a predetermined image process on an electric signal subjected to the demodulation process. Furthermore, the receiving apparatus 5 includes a control unit 26 configured like a micro computer having a CPU or the like responsible for the control of the entire receiving apparatus 5. To the control unit 26 are connected not only the A/D converting unit 22, the antenna switching unit 23, and the image processing circuit 25, as described above, but also a power switch 27, an interface 28 serving as a data input/output unit, and the portable recording medium 9 serving as the storage unit for storing the image data and the like. Moreover, an output side of the demodulator 24 is branched and connected to the interface 28, which is connected to a cable connector 29, to which the viewer cable 6 is connected, whereby data can be output from the demodulator 24 to the viewer 7 via the viewer cable 6. In addition, the interface 28 is connected to the control unit 26, and therefore, the data from the viewer 7 can be input into the control unit 26 via the viewer cable 6. To the control unit 26 is further connected a viewer connection detecting unit 30 for detecting the connection of the viewer 7. The viewer connection detecting unit 30 detects the electric connection between the receiving apparatus 5 and the viewer 7 through the connection between the viewer cable 6 and the cable connector 29. The viewer cable 6 includes a plurality of data lines, and further, the receiving apparatus 5 includes a built-in battery for driving each of the component parts or has a battery connected from the outside, although not illustrated in particular.

The viewer 7 includes a cable connector 33 to which the viewer cable 6 is connected, an interface 34 serving as an input/output unit connected to the cable connector 33, and the image processing circuit 35 serving as an identification data generator (image processor) which is connected to the interface 34 and generates the identification data. The viewer 7 is further provided with the display unit 11, the power switch 12, the marking button 13 serving as the marker, a built-in memory 36, and a control unit 38 having the configuration like a micro computer provided with a CPU or the like responsible for the control of the entire viewer 7. To the control unit 38 are connected not only the interface 34 and the image processing circuit 35, as described above, but also the display unit 11, the power switch 12, and the built-in memory 36. To the control unit 38 is connected a receiving apparatus connection detecting unit 37 for detecting the connection to the receiving apparatus 5. The receiving apparatus connection detecting unit 37 detects the electric connection between the receiving apparatus 5 and the viewer 7 through the connection between the viewer cable 6 and the cable connector 33. The viewer 7 includes a battery for driving each of the component parts, although not illustrated in particular. Alternatively, the viewer 7 may be provided with an antenna or a receiving unit for receiving a radio signal directly from the outside.

The image processing circuit 35 has both of the function as the identification data generator and the function as the image processor, thereby subjecting the demodulated electric signal (image data) to a predetermined image processing, for example, not only a normal image processing for displaying the image data of the subject 1 on the display unit 11 but also another image processing for determining a ratio of red data contained in the image data so as to detect the image suspected of showing pathological lesion such as the hemorrhage, and thus obtaining the image processing result. The above-described image processing circuit 35 includes an image processing circuit unit for detecting the image suspected of showing pathological lesion such as the hemorrhage, so as to generate identification data corresponding to the image processing result.

The image processing circuit 35 further has the function as the identification data generator that generates the identification data concerning a reception status of the image data of the subject 1. The above-described image processing circuit 35 includes the image processing circuit unit for generating the identification data concerning the reception status of the image data of the subject 1 displayed on the display unit 11, thereby generating the identification data concerning the reception status based on a received electric field strength when the receiving apparatus 5 receives the image data from the capsule endoscope 2. Examples of the identification data concerning the reception status include information indicating the reception status of the receiving apparatus 5 for receiving the image data from the capsule endoscope 2 in the subject 1, information indicating the connection state between the receiving apparatus 5 and the viewer 7 (the state in which the receiving apparatus 5 and the viewer 7 can communicate with each other via the viewer cable 6), and positional information on the capsule endoscope 2 in the subject 1 based on the received electric field strength upon the receipt of the image data. One or more pieces of identification data (the identification data recognizable in the work station 8) generated by the image processing circuit 35 are displayed on the display unit 11 in a predetermined display pattern.

The control unit 38 having the function as a display controller allows the image data subjected to the image processing to be displayed in the image display area 11a of the display unit 11, allows the predetermined display pattern as the identification data resulting from the image processing to be displayed as the image mark 11b on the display unit 11, and allows the predetermined display pattern as the identification data on the reception status to be displayed as the reception status mark 11c on the display unit 11. Moreover, the control unit 38 generates information indicating the marking result (identification data corresponding to the marking result), with respect to the image data of the subject 1 displayed on the display unit 11 every time it detects an electric signal generated by the depression of the marking button 13. In other words, the control unit 38 functions as the identification data generator for generating the identification data corresponding to the marking result. The above-described control unit 38 transmits, to the receiving apparatus 5, the identification data corresponding to the marking result and the various identification data produced by the image processing circuit 35, as required. In this case, the control unit 38 outputs, for example, both of the information indicating the marking result and the information indicating the image processing result to the receiving apparatus 5 via the interface 34.

Here, the image processing circuit 35 and the control unit 38 having the identification data producing function are so configured as to be able to transmit the identification data thus generated to the portable recording medium 9 (the portable recording medium 9 in a state attached to the receiving apparatus 5), having the function of a recording unit in the receiving apparatus 5. Specifically, the image processing circuit 35 transmits the generated identification data to the control unit 38. In this case, the control unit 38 transmits the identification data generated by the image processing circuit 35 to the receiving apparatus 5 via the interfaces 28, 34, and the like. In addition, the control unit 38 transmits the identification data concerning the reception status to the receiving apparatus 5 via the interfaces 28, 34, and the like, every time the control unit 38 generates the identification data on the reception status. The control unit 26 in the receiving apparatus 5 controls the portable recording medium 9 so that various kinds of identification data received from the control unit 38 via the interfaces 28, 34, and the like are recorded in the portable recording medium 9 in association with the image data. The image processing circuit 35 and the control unit 38 transmit (record) the identification data to (or in) the portable recording medium 9 in the receiving apparatus 5, as described above, whereby the identification data can be added to the image data in the portable recording medium 9.

Incidentally, the viewer 7 may be so configured as to take in the image processed by the image processing circuit 25 in the receiving apparatus 5 and the image processing result. That is to say, the image processing circuit 25 in the receiving apparatus 5 may have the function as the identification data generator which generates the identification data, similarly to the above-described image processing circuit 35 in the viewer 7. For example, the image processing circuit 25 in the receiving apparatus 5 may subject the demodulated image data not only to a predetermined image processing such as the normal image processing for displaying the image data on the subject 1 on the display unit 11 but also another image processing for determining the ratio of the red data contained in the image data so as to detect the image suspected of showing pathological lesion such as the hemorrhage, and generate the identification data corresponding to the image processing result. The control unit 38 may display, on the display unit 11, both of the predetermined display pattern as the identification data generated by the image processing circuit 25 in the receiving apparatus 5 and the image data on the subject 1. In this case, it becomes unnecessary to provide the image processing circuit 35, whereby the number of component parts constituting the viewer 7 is reduced, so as to achieve miniaturization and cost reduction.

Alternatively, both of the image processing circuit 25 in the receiving apparatus 5 and the image processing circuit 35 in the viewer 7 may have the function of the identification data generator, and share the operation according to the connection state between the receiving apparatus 5 and the viewer 7. In other words, the viewer connection detecting unit 30 and the receiving apparatus connection detecting unit 37 may detect the electric connection (the communication connection) between the receiving apparatus 5 and the viewer 7 via the viewer cable 6, and change the share of the operations of the image processing circuits 25 and 35 according to the connection state between the receiving apparatus 5 and the viewer 7, as described above.

Specifically, when the receiving apparatus 5 and the viewer 7 are not in communication connection, the control unit 26 controls the image processing circuit 25 in such a manner as to subject the image data on the subject 1 to the normal image processing for displaying the image on the display unit 11 and the above-described image processing for generating the identification data. When the receiving apparatus 5 and the viewer 7 are in communication connection, the viewer connection detecting unit 30 detects the communication connection between the receiving apparatus 5 and the viewer 7, and notifies the control unit 26 of the detection result. The control unit 26 controls the image processing circuit 25 based on the result detected by the viewer connection detecting unit 30 in such a manner as to subject the image data to the image processing for generating the identification data out of the above-described image processings. In this case, the receiving apparatus connection detecting unit 37 detects the communication connection between the receiving apparatus 5 and the viewer 7 in a similar manner, and notifies the control unit 38 of the detection result. The control unit 38 controls the image processing circuit 35 based on the detection result from the receiving apparatus connection detecting unit 37 in such a manner as to subject the image data to the normal image processing for forming the display image of the display unit 11 out of the above-described image processings (other image processing which has not been performed yet by the image processing circuit 25). In this manner, the image processing circuits 25 and 35 can mutually share the processing operation according to the connection state between the receiving apparatus 5 and the viewer 7, thus performing each of the various kinds of image processings.

Figure 4:
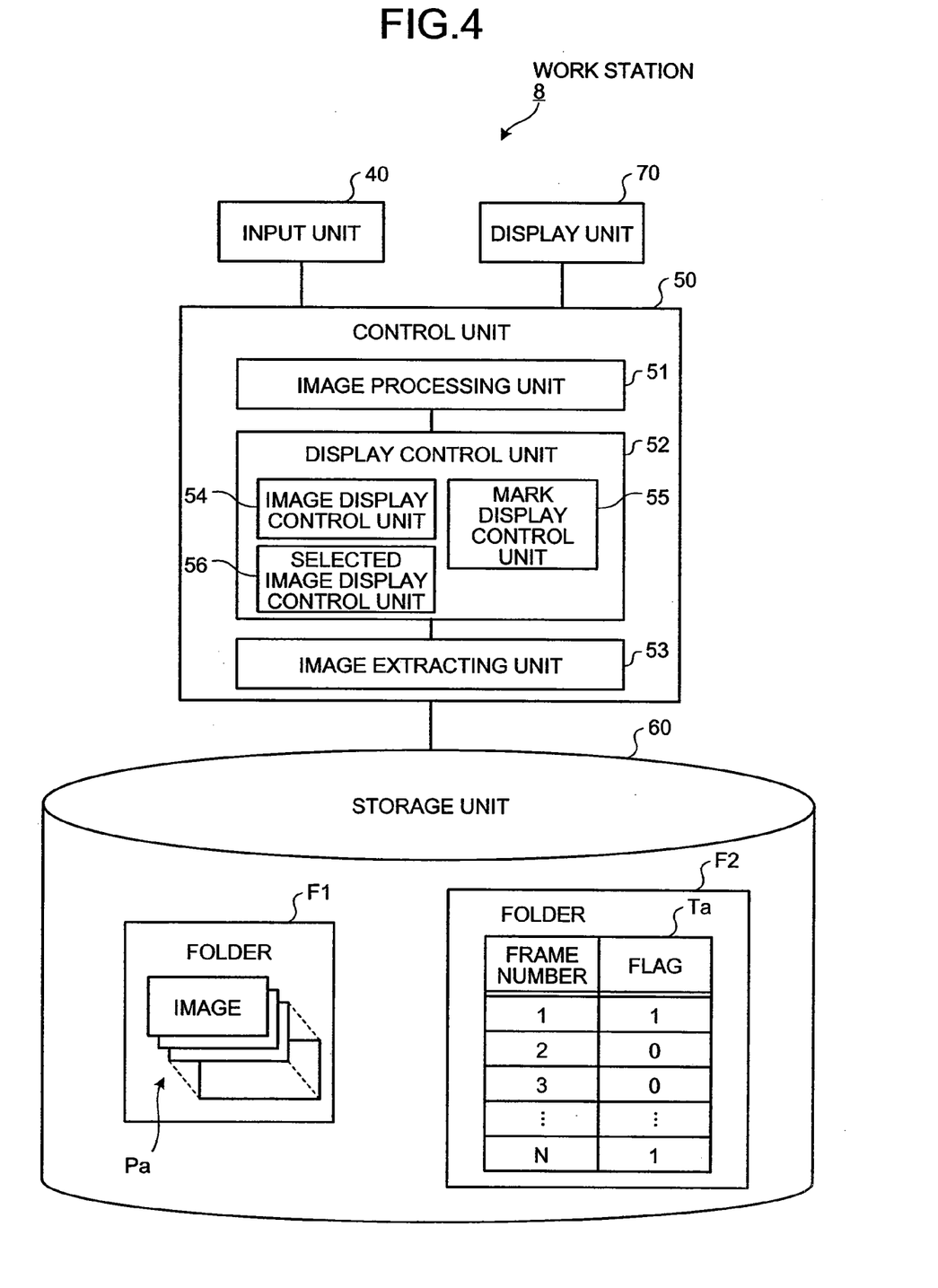
FIG. 4 is a schematic block diagram illustrating a constitutional example of a work station in the first embodiment.

Next, the inside configuration of the work station 8 will be described with reference to a schematic block diagram of FIG. 4. In FIG. 4, the work station 8 is provided with an input unit 40, a control unit 50, a storage unit 60, and a display unit 70. The input unit 40 is implemented with a pointing device such as a key board and a mouse, so as to receive an operation instruction for the work station 8 and instruction information on the processing performed by the work station 8, and to deliver each piece of the instruction information to the control unit 50.

The storage unit 60 is implemented with, for example, a hard disk device, and stores various types of images. For example, the storage unit 60 includes folders F1 and F2. In the folder F1, an image group Pa consisting of images picked up by the capsule endoscope 2 is stored. A frame number and a time are applied to each of the images in the image group Pa stored in the folder F1 according to the order of the reception of the image data in the receiving apparatus 5. On the other hand, in the folder F2, the frame numbers of the images in the image group Pa and flags indicating corresponding body-cavity images are stored in association with each other based on the information indicating the result of image processing by the image processing circuit 35 in the viewer 7. Here, the frame numbers of the body-cavity images are from 1 to N (N is an arbitrary positive number) in an order of the image pick-up, and further, a flag "1" is added to the frame number of the body-cavity image (e.g., the image suspected of showing pathological lesion) obtained as a result of image processing by the image processing circuit 35. Moreover, a flag (not shown) indicating the pertinent body-cavity image is stored in association with each of the frame numbers of the images in the image group Pa based on the information indicating the result of marking by the marking button 13 in the same manner as described above. Alternatively, the input unit 40 may be equipped with a similar function to that of the marking button, so that a desired body-cavity image can be selected through a manipulation of a cursor displayed on a screen.

The display unit 70 is implemented with a CRT display, a liquid crystal display, or the like, and displays the instruction information supplied from the input unit 40 or a result of instruction. Furthermore, the display unit 70 has an image display region, in which the body-cavity image included in the image group Pa stored in the folder F1 of the storage unit 60, a mark 73 indicating an image designated as a result of image processing, a reduced image (thumbnail image) designated based on a result of marking, and the like are displayed. In other words, the display unit 70 has a display screen on which an image display region (window) W is displayed similarly to an example of a display screen of FIG. 8. The window W mainly includes a body-cavity image display region A1, in which the body-cavity image is displayed, a thumbnail image display region A2, in which a thumbnail image Pc is displayed, and an identification information display region A3, in which identification information such as an examination ID and a patient ID is displayed. The thumbnail image display region A2 is arranged at a region below the body-cavity image display region A1; the identification information display region A3 is arranged at a region left to the body-cavity image display region A1; and a group of buttons such as a play button 71 employed to control the display of moving images, a time bar 72, and the mark 73 are displayed in a region between the body-cavity image display region A1 and the thumbnail image display region A2.

Figure 8:
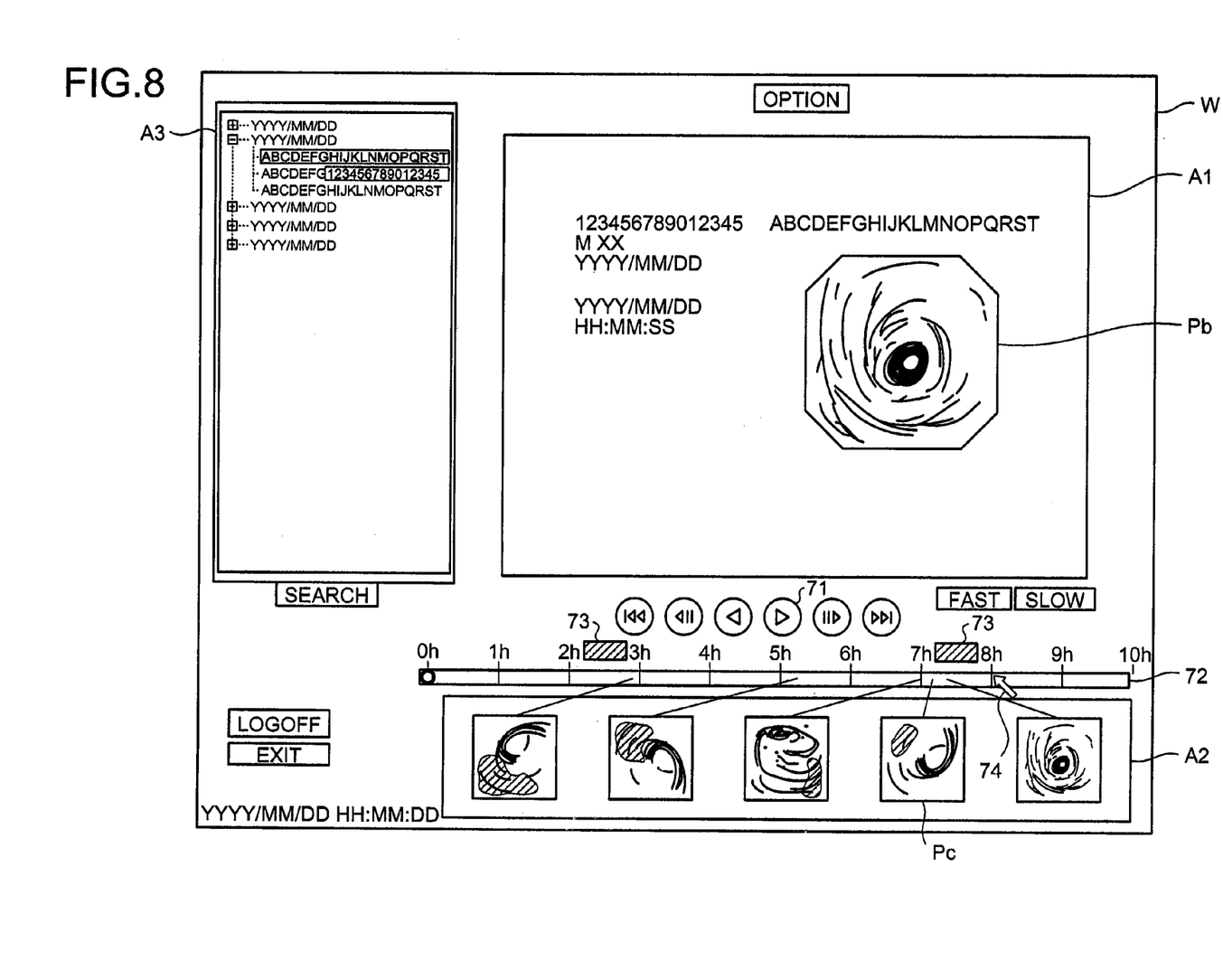
FIG. 8 is a diagram illustrating one example of a display screen of a display in the work station.

In the body-cavity image display region A1, body-cavity images included in the image group Pa stored in the folder F1 are sequentially displayed at a desired play frame rate (display rate for reproducing the images). The time bar 72 indicates a length of time, during which the body-cavity images are picked up in the subject. In the first embodiment, time used for image pick-up is assumed to be ten hours. The time bar 72 also shows a time when an image currently displayed in the body-cavity image display region A1 is picked up. The time bar 72 and a selected thumbnail image displayed in the thumbnail image display region A2 are linked to each other via a connection line based on time information added to the body-cavity image Pb. The mark 73 is displayed in such a manner so as to indicate the time required for picking up the corresponding body-cavity image on the time bar 72.

The control unit 50 controls the processing or operation of each of the input unit 40, the storage unit 60, and the display unit 70. The control unit 50 includes an image processing unit 51, a display control unit 52, and an image extracting unit 53. The image processing unit 51 processes the image in the image group Pa, and further, creates a table Ta, in which the frame numbers of the images in the image group Pa and the flags are associated with each other. Moreover, the image processing unit 51 adds a flag indicating that the image is a thumbnail image to the frame number of the pertinent image based on the instruction information supplied from the input unit 40 to output the table Ta. For example, the flag "1" indicates that the image is marked as a result of image processing, whereas the flag "0" indicates that the image is not marked.

The display control unit 52 has the function of controlling the display processing in the display unit 70, and includes an image display control unit 54 serving as an image display controller that controls the image display processing, a mark display control unit 55 that controls the display processing with respect to the mark and the time on the time bar, and a selected image display control unit 56 that controls the display processing with respect to a selected image. The image display control unit 54 allows the body-cavity images in the image group Pa to be displayed on the display unit 70 in the order of the frame numbers in the body-cavity image display region A1 based on the information on the image group Pa stored in the folder F1 and the table Ta stored in the folder F2.

The mark display control unit 55 allows the time required for taking in all the images to be displayed on the time bar 72 which is the time display region of the display unit 70, and further, allows the mark 73 indicating the time required for picking up the body-cavity image obtained as a result of image processing to be displayed on the time bar 72. In the first embodiment, a default value of the time bar 72 is set to 10 hours.

The image extracting unit 53 extracts a body-cavity image, which is designated based on the instruction information supplied from the input unit 40, from the image group Pa stored in the folder F1. The selected image display control unit 56 allows the thumbnail image which is a reduced image of the body-cavity image extracted from the image group Pa by the image extracting unit 53 to be displayed in the order of the frame numbers in the thumbnail image display region A2. In addition, the selected image display control unit 56 allows the time bar 72 and the thumbnail image displayed in the thumbnail image display region A2 to be linked to each other via the connection line based on the time information added to the body-cavity image Pb.

Next, the operation of a radio-type intra-subject information acquiring system including the image display system will be described with reference to flowcharts of FIGS. 5 to 7. Here, information on the above-described result of image processing may be referred to as image processing information, and further, information on the above-described result of marking may be referred to as marking information.

Figure 5:
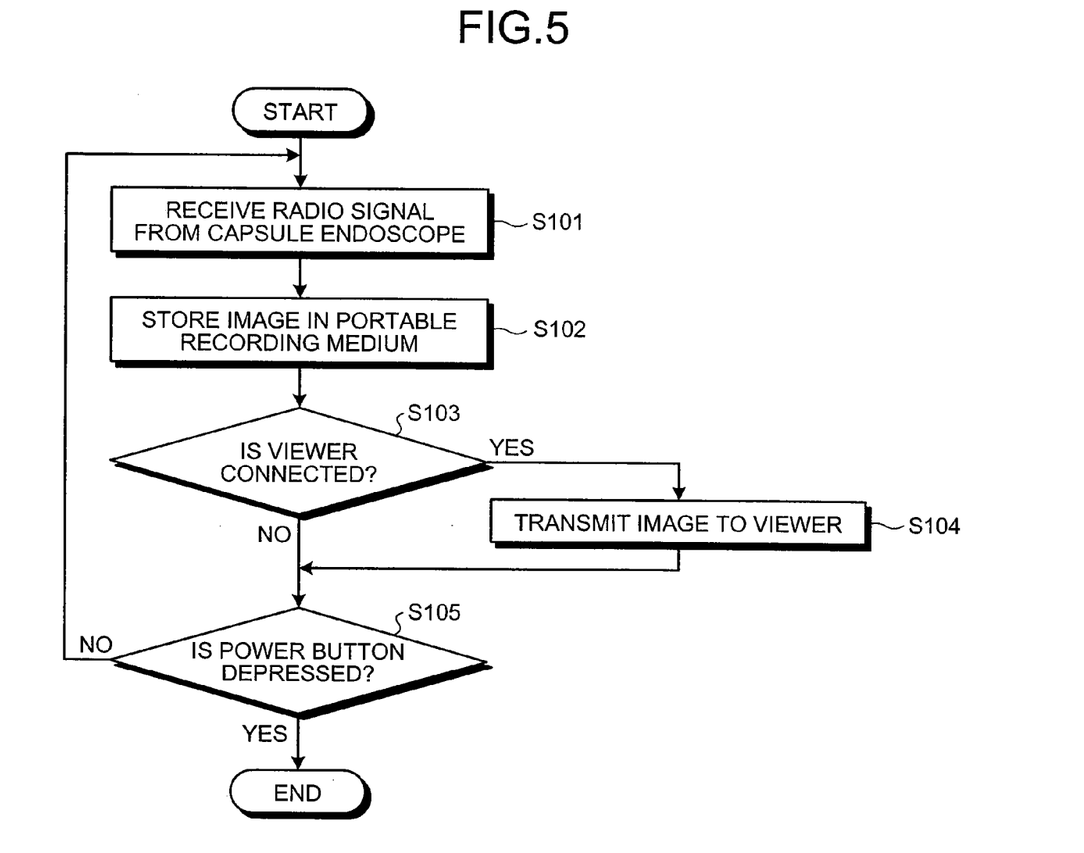
FIG. 5 is a flowchart illustrating an operation of the receiving apparatus.

FIG. 5 is a flowchart illustrating the operation of the receiving apparatus 5. In FIG. 5, when the receiving apparatus 5 receives the radio signal from the capsule endoscope 2 via the receiving antennas 4a to 4h (step S101), the image is stored in the portable recording medium 9 consisting of the compact flash (registered trademark) memory after the image demodulation by the demodulator 24 and the image processing by the image processing circuit 25 (step S102). The portable recording medium 9 having the image data stored therein is taken from the receiving apparatus 5, and inserted in the work station 8, in which the image data can be taken out and displayed, as described later. Next, upon receipt of the detection signal from the viewer connection detecting unit 30, the control unit 26 determines as to whether or not the viewer 7 is connected (step S103).

If it is determined in step S103 that the viewer 7 is connected (Yes in step S103), the image stored in the portable recording medium 9 is transmitted to the viewer 7 (step S104). In contrast, if the viewer 7 is not connected (No in step S103), it is determined as to whether or not the power switch 12 is depressed (step S105).

If the power switch 27 is not depressed in step S105 (No in step S105), it is determined that the radio signal is transmitted from the capsule endoscope 2, and then, the control routine returns to step S101, in which the receiving apparatus 5 receives the radio signal from the capsule endoscope 2, and repeats the above described operation. If the power switch 27 is depressed (Yes in step S105), it is determined that the transmission of the radio signals of all the images from the capsule endoscope 2 is completed, and the operation ends.

Figure 6:
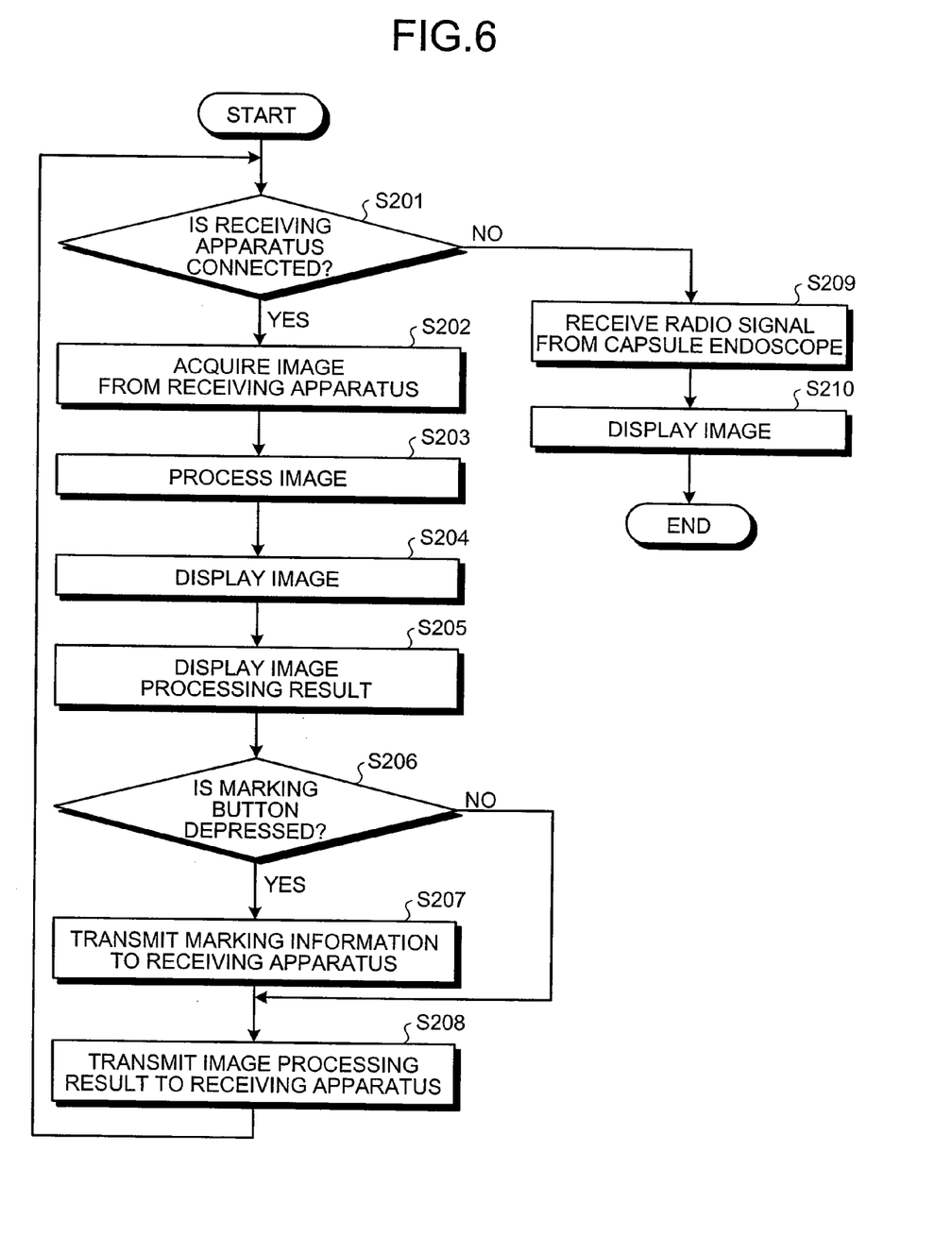
FIG. 6 is a flowchart illustrating an operation of the viewer.

FIG. 6 is a flowchart illustrating the operation of the viewer 7. FIG. 6 shows the case where the viewer 7 is provided with a receiving antenna or a receiving unit for receiving the radio signal directly from the outside. In the viewer 7 of FIG. 6, the control unit 38 receives the detection signal from the receiving apparatus connection detecting unit 37, and determines as to whether or not the receiving apparatus 5 is connected (step S201).

If it is determined in step S201 that the receiving apparatus 5 is connected (Yes in step S201), the image data is acquired from the receiving apparatus 5 via the interface 34 (step S202), and then, the image processing circuit 35 performs the image processing, thereby obtaining the result of the image processing (step S203). Next, the control unit 38 displays the processed image (i.e., the body-cavity image of the subject 1) at the image display area 11a of the display unit 11, and further, displays the result of the image processing as the image mark 11b on the display unit 11 (steps S204 and S205). Subsequently, the control unit 38 determines as to whether or not the marking button 13 is depressed (step S206).

If it is determined in step S206 that the marking button 13 is depressed (Yes in step S206), the control unit 38 marks the image data suspected of showing pathological lesion, for example, out of the image data on the subject 1 displayed on the display unit 11 (marking step), and transmits the marking information and the information on the image processing result (i.e., the above-described identification data) to the receiving apparatus 5 (steps S207 and S208). If it is determined that the marking button 13 is not depressed (No in step S206), the control unit 38 transmits only the information on the image processing result to the receiving apparatus 5 (step S208). The marking information and the image processing information are transmitted to the receiving apparatus 5 in association with the frame number of the image, for example, so that the control unit 26 in the receiving apparatus 5 can store the marking information and the image processing information in the portable recording medium 9 while associating them with the frame number of the image.

If it is determined in step S201 that the receiving apparatus 5 is not connected (No in step S201), the receiving unit receives the radio signal from the capsule endoscope 2 via the receiving antenna not shown (step S209), and the received image is displayed on the display unit 11 (step S210). In the case where there is no radio function, and the receiving apparatus 5 is not connected (No in step S201), the above-described operation is completed immediately.

In the procedures illustrated in FIG. 6, the control unit 38 transmits the identification data corresponding to the image processing result of the image processing circuit 35 to the receiving apparatus 5, and the control unit 26 in the receiving apparatus 5 stores the identification data in the portable recording medium 9 while associating the data with the image data. However, the procedures are not limited to the above-described procedures. For example, the control unit 38 may transmit the identification data on the reception status to the receiving apparatus 5, and the control unit 26 in the receiving apparatus 5 may store the identification data on the reception status in the portable recording medium 9 while associating the data with the image data.

Alternatively, the image processing circuit 35 in the viewer 7 may produce identification data corresponding to the image processing result of the image data suspected of showing pathological lesion, and may add the identification data to the marked image data if the image data is marked through the operation of the marking button 13. Alternatively, the image processing circuit 35 may add the identification data to the image data every time the image processing circuit 35 produces identification data corresponding to the image processing result of the image data suspected of showing pathological lesion irrespective of the marking result with respect to the image data. This also applies to the image processing circuit 25 in the receiving apparatus 5.

As described above, in the first embodiment, the image processing circuit 35 performs the image processing on the image data input from the receiving apparatus 5 via the interface 34, and thereafter, the control unit 38 allows the image and the image processing result to be displayed on the display unit 11 based on the image processing result of the image data. As a consequence, a user can observe the body-cavity image in real time referring to the processing result of the image processing displayed on the display, thereby preventing any oversight of the image having the predetermined image processing result (such as the image suspected of showing pathological lesion such as the hemorrhage).

In addition, in the first embodiment, the user can pick up an image which attracts his/her attention by depressing the marking button 13 during real-time observation. As a consequence, failure of the user to pick up an image which attracts his/her attention during the main observation on the work station can be prevented, and at the same time, it is possible to save time and trouble in picking up the image during the main observation of the image on the work station.

The in-vivo image display apparatus according to the invention can arbitrarily produce the identification data, which corresponds to the image data on the subject 1 displayed on the display unit 11 and can be recognized in the work station. Consequently, it is possible to produce the identification data on an abnormal image (such as the image suspected of showing pathological lesion) among the images of the interior of the subject 1 displayed on the display unit 11, whereby it is possible to notify on another observation apparatus such as the work station 8 that the abnormal image is displayed, and a work required for image diagnosis can be alleviated.

Modification

Figure 7:
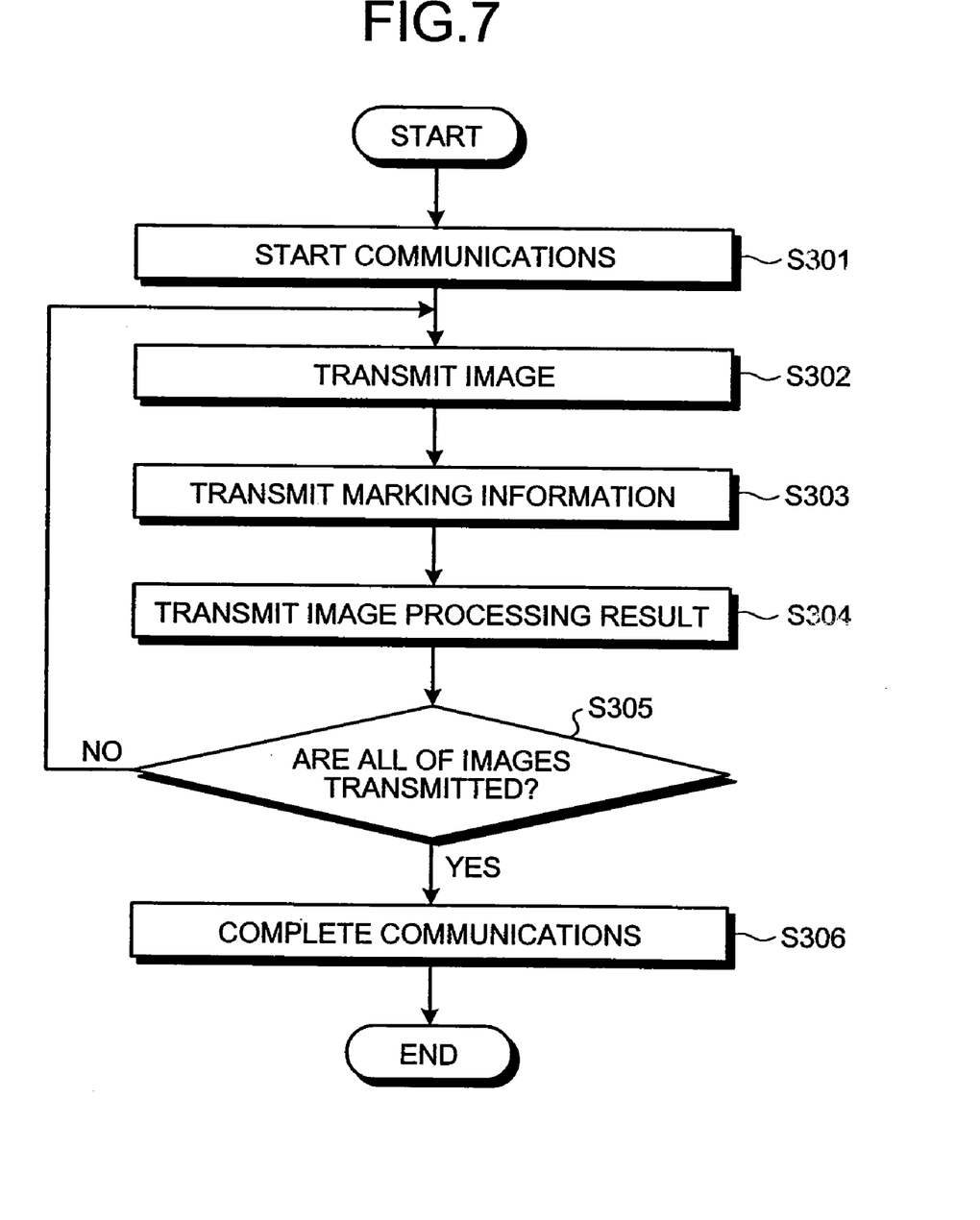
FIG. 7 is a flowchart illustrating a modification of the operation of the receiving apparatus.

FIG. 7 is a flowchart illustrating a modification of the operation of the receiving apparatus. Explanation will be made below on the present modification, in which the data is transferred between the receiving apparatus 5 and the work station 8 via a cable or by radio in place of the portable recording medium 9. Referring to FIG. 7, when the receiving apparatus 5 starts to communicate with the work station 8 (step S301), the control unit 26 starts to transmit an image (step S302). Next, the control unit 26 transmits the marking information and the information on the image processing result taken from the viewer 7 (steps S303 and S304). Thereafter, the control unit 26 determines as to whether or not data on all the images are transmitted (step S305).

If it is determined in step S305 that the data on all the images are not transmitted (No in step S305), the control routine returns to step S302, and the image is transmitted again. When the data on all the images are transmitted (Yes in step S305), the communications with the work station 8 end (step S306).

In this manner, the present modification can achieve the same effect as that achieved in the first embodiment. Furthermore, the receiving apparatus 5 and the work station 8 are connected to each other via the cable or by radio, the viewer performs the image processing, and the image and the image processing result are copied to and downloaded in the work station during the real-time observation in the present modification. As a consequence, it is possible to shorten an image processing time at the time of downloading, and further, the main observation on the work station can be performed immediately after the real-time observation without delay.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

As described above, the in-vivo image display apparatus, the receiving apparatus, and the image display system using the in-vivo image display apparatus and the receiving apparatus, and an image display method according to the invention are useful to a medical observation apparatus which is inserted inside a human body for an observation of an examined site, and particularly, are suitable for alleviating the image diagnosing work on the work station or the like.

What is claimed is:

1. An image display system comprising:
   a receiving apparatus which sequentially receives image data acquired by an in-vivo image acquiring apparatus and stores the image data received in a recording unit; and an in-vivo image display apparatus which sequentially takes in the image data from the receiving apparatus, and sequentially displays the image data taken-in on a display unit;
   wherein each of the receiving apparatus and the in-vivo image display apparatus includes an identification data generator capable of arbitrarily generating identification data which corresponds to the image data displayed on the display unit and can be recognized in another in-vivo image display apparatus, and
   wherein the receiving apparatus and the in-vivo image display apparatus include a connection detecting unit which detects a cable connection between the receiving apparatus and the in-vivo image display apparatus, and changes operation sharing between the identification data generator included in the receiving apparatus and the identification data generator included in the in-vivo image display apparatus.

2. The image display system according to claim 1, wherein the in-vivo image display apparatus includes a marker which arbitrarily marks image data suspected of showing pathological lesion out of the image data displayed on the display unit, and
   the identification data generator includes an image processing circuit unit which performs image processing to detect the image data suspected of showing pathological lesion out of the image data displayed on the display unit, and generates the identification data corresponding to a result of the image processing.

3. An image display method for displaying an image on an in-vivo image display apparatus, comprising:
   sequentially receiving image data acquired by an in-vivo image acquiring apparatus using a receiving apparatus, and storing the image data received in a recording unit; and
   sequentially taking in the image data from the receiving apparatus into an in-vivo image display apparatus, and sequentially displaying the image data taken-in on a display unit;
   arbitrarily generating identification data which corresponds to the image data displayed on the display unit and can be recognized by another in-vivo image display apparatus using at least one of the receiving apparatus and the in-vivo image display apparatus, and
   detecting a cable connection between the receiving apparatus and the in-vivo image display apparatus using a connection detecting unit provided in the receiving apparatus and the in-vivo image display apparatus, and changing operation sharing of whether to generate the identification data by the receiving apparatus or to generate the identification data by the in-vivo image display apparatus.

4. The image display system according to claim 1, wherein the identification data generator performs normal image processing, image processing for generating identification data, or both, according to the result of detection by the connection detecting unit.

* * * * *